United States Patent [19]

Bailey et al.

[11] Plant 4,740

[45] Jun. 9, 1981

[54] APPLE TREE—N.J. 49 CULTIVAR

[75] Inventors: Catherine H. Bailey, Englishtown; L. Fredric Hough, Bloomsbury, both of N.J.

[73] Assignee: Stark Brothers Nurseries & Orchards Company, Louisiana, Mo.

[21] Appl. No.: 125,578

[22] Filed: Feb. 28, 1980

[51] Int. Cl.[3] ..... A01H 5/03

[52] U.S. Cl. ..... Plt./34

[58] Field of Search ..... Plt./34

*Primary Examiner*—Robert E. Bagwill

*Attorney, Agent, or Firm*—Burns, Doane, Swecker & Mathis

[57] ABSTRACT

A new and distinct apple variety which originated by the crossing of an unnamed New Jersey seedling No. 109055 (non-patented) with pollen from the Mollies Delicious cultivar (non-patented) is provided. This new apple variety can be distinguished by the early maturing characteristic of its large conic shaped fruit which has an attractive bright red skin color (as illustrated). Also, the new variety produces more uniformly sized fruit than the pollen parent Mollies Delicious cultivar. The fruit flesh is white to cream in color and similar to Mollies Delicious cultivar in flavor.

SUMMARY OF THE INVENTION

The new and distinct variety of apple tree originated through the hand pollination of unnamed New Jersey seedling No., 109055 (non-patented) with the pollen from Mollies Delicious cultivar (non-patented) at Cream Ridge, N.J. The resulting seed from these hand pollinated flowers was germinated in a greenhouse during the winter of 1964–1965. The germinated seedlings were then planted out-of-doors the following spring in block D-2 at the New Jersey Agricultural Experiment Station at Cream Ridge, N.J. Tree 79 in row 42 of this planting first fruited in 1971 and was selected for its fruit size, shape, color, and substantially earlier season of maturity.

Trees of the new variety have exhibited a strong and vigorous growth habit and the ability to produce fruit similar to that of the Mollies Delicious cultivar, its pollen parent. The fruit is large in size and conic shaped and can be distinguished from that of the Mollies Delicious cultivar by (1) a substantially earlier ripening characteristic, (2) a more uniform size, and (3) a more attractive bright red appearance (as illustrated). The fruit commonly ripens in mid-summer or approximately four weeks prior to the Red Delicious-Mood cultivar when observed at Cream Ridge, N.J. When grown at other locations the disparity in ripening times may be even greater. The flesh of the fruit is white to cream in color (as illustrated) and is similar to that of the Mollies Delicious cultivar in flavor and texture.

Asexual propagation of the new variety was first carried out in the spring of 1972 when it was grafted into trees 35 and tree 36 of row 65 in block D-2 at the New Jersey Agricultural Experiment Station at Cream Ridge, N.J. This and subsequent asexual propagations have demonstrated that its combination of characteristics comes true to form and is established and transmitted through succeeding generations.

The specimens described herein were grown and observed at Cream Ridge, N.J.

The new variety has been named in N.J. 49 cultivar.

BRIEF DESCRIPTION OF THE PHOTOGRAPH

The accompanying photograph shows typical specimens of the fruit and foliage of the new variety in color as nearly true as it is reasonably possible to make the same in a color illustration of this character.

DETAILED DESCRIPTION OF THE NEW VARIETY

Dates of first and last pickings: August 20 and September 9.

Tree: Medium; vigorous; spreading, rapid growing; productive.

Trunk: Medium stocky; medium smooth.

Branches: Medium thick; smooth; much branching; red.

Leaves: Oval; abruptly pointed; medium thick; medium dark green; smooth; pubescence on the underside.

*Length.*—Approximately $3\frac{1}{2}$ inches.

*Width.*—Approximately $1\frac{7}{8}$ inches.

*Margin.*—Crenate; serrate.

*Petiole.*—Medium long; medium thick.

Flowers:

*Date of first bloom.*—April 23.

*Date of last bloom.*—April 26.

Fruit:

*Maturity when described.*—Hard ripe; date—August 24.

*Size.*—Uniform. Axial diameter: approximately $2\frac{3}{4}$ to $3\frac{1}{2}$ inches. Transverse in suture planes: approximately 3 to $3\frac{1}{2}$ inches.

*Form.*—Conic shaped.

*Cavity.*—Symmetrical; acute; russet present. Depth: approximately $\frac{5}{8}$ to $\frac{3}{4}$ inch. Breadth: approximately 1 to $1\frac{1}{4}$ inch. Markings: russet.

*Basin.*—Symmetrical; slightly furrowed. Depth: approximately $\frac{1}{2}$ inch. Breadth: approximately $\frac{3}{4}$ to 1 inch. Markings: none.

*Stem.*—Length: approximately 1 inch. Breadth: approximately 3/32 to 4/32 inch.

*Calyx.*—Open; persistent; acute; separated; approximate; erect; converged from base toward center. Length: approximately $\frac{1}{4}$ to 5/16 inch. Outer-surface: pubescent. Inner-surface: pubescent.

*Eye.*—Medium large; partially closed.

*Skin.*—Smooth; glossy; dots conspicuous which are few, small, depressed, circular, and angular. Color of dots: white. Distribution of dots: all over—heavier at basin. Ground color: Citron Yellow, Plate XVI, Color No. 23′, tone b of Ridgway's Color Standards. Color of markings: striped to blushed with Brazil Red, Plate I, Color No. 5.00R, tone i. Bloom: moderate. Scarfskin: wanting.

*Flesh.*—Juicy. Color: white with yellowish greenish tint. Texture: fine. Flavor: mild.

*Core.*—Sessile. Bundle area (longitudinal section): medium large; broadly ovate. Bundle color: green-yellowish. Dots: conspicuous in one or more whirls. Alternate bundle: reaches to stamen. Core lines: clasping; in cross-section distinct. Carpellary area: distinct. Calyx tube: glabrous; urn-shaped. Depth of tube to shoulder: approximately 3/16 inch. Entire depth: approximately 5/16 to $\frac{3}{8}$ inch. Styles: present; distinct toward base; pubescent. Stamens: one; distinct; whorls median. Seed cells: partially open. Surface: tufted.

*Seeds.*—Number perfect—6; number imperfect—2. Number in one cell: 2. Length: approximately 5/16 inch. Breadth: approximately 5/32 inch. Form: acute. Color: brown.

Use: Local—dessert.

Keeping quality: Medium.

Resistance to:

*Insects.*—Medium.

*Diseases.*—Medium.

1 Drawing Figure

1

We claim:

1. A new and distinct variety of apple tree, substantially as illustrated and described, characterized by its general similarity to the pollen parent Mollies Delicious cultivar, but being distinct therefrom by the ability to

2 form fruit which (1) ripens substantially earlier, (2) is of a more uniform size, and (3) is of a more attractive bright red appearance.

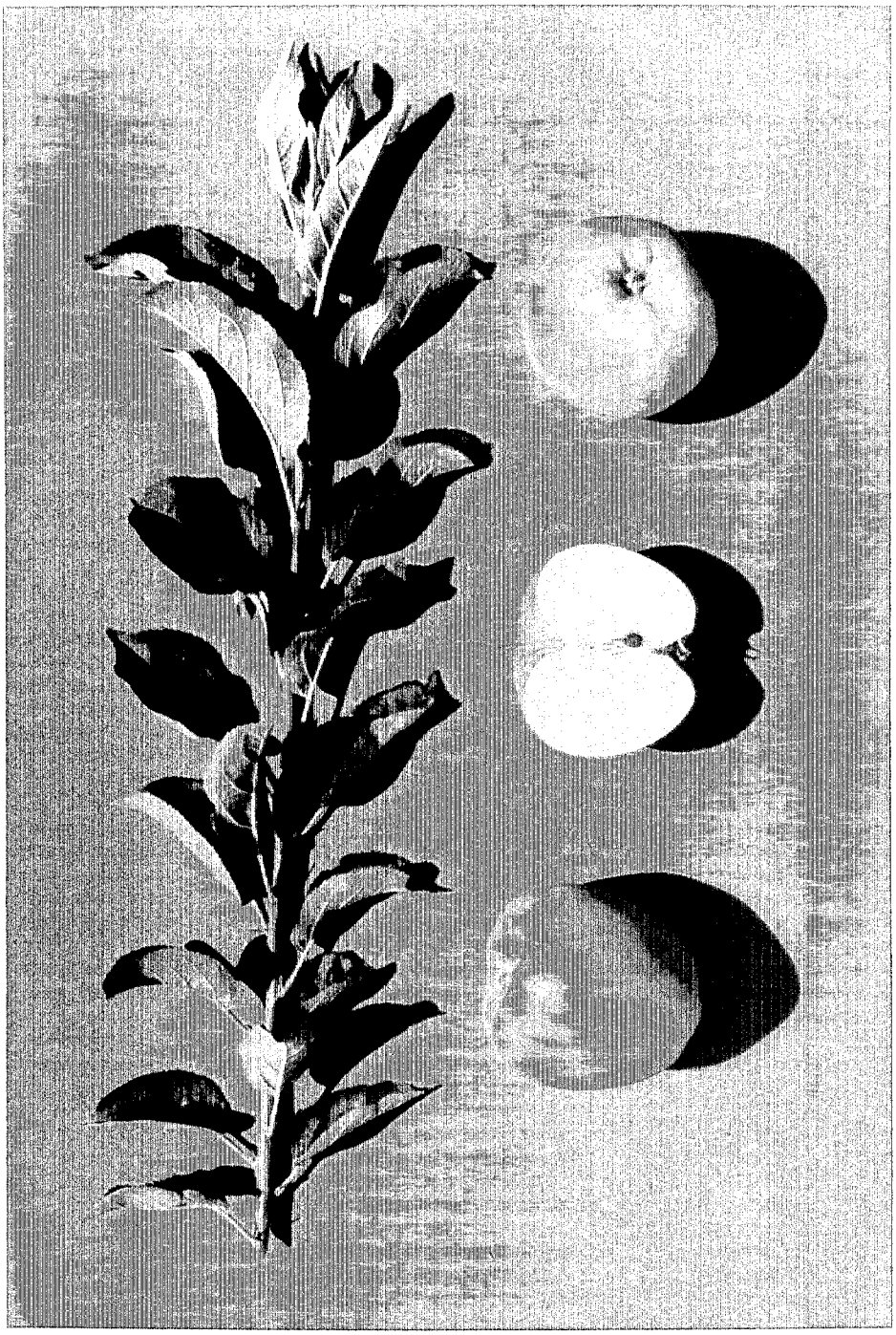

* * * * *